(12) United States Patent
Christie

(10) Patent No.: US 8,182,490 B2
(45) Date of Patent: May 22, 2012

(54) ADJUSTABLE ANGLE TARGETING DEVICE FOR AN INTRAMEDULLARY NAIL AND METHOD OF USE

(75) Inventor: Charles D. Christie, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1006 days.

(21) Appl. No.: 12/143,443

(22) Filed: Jun. 20, 2008

(65) Prior Publication Data

US 2009/0318926 A1   Dec. 24, 2009

(51) Int. Cl.
*A61B 17/58* (2006.01)
(52) U.S. Cl. ............................................ 606/98; 606/62
(58) Field of Classification Search ............... 606/62, 606/96, 98
See application file for complete search history.

(56) References Cited

U.S. PATENT DOCUMENTS

| | | | |
|---|---|---|---|
| 4,103,683 A | 8/1978 | Neufield | |
| 4,541,424 A | 9/1985 | Grosse et al. | |
| 4,622,959 A | 11/1986 | Marcus | |
| 4,667,664 A | 5/1987 | Taylor et al. | |
| 4,848,327 A | 7/1989 | Perdue | |
| 5,295,991 A | 3/1994 | Frigg | |
| 5,346,496 A | 9/1994 | Pennig | |
| 5,411,504 A | 5/1995 | Vilas | |
| 5,620,449 A | 4/1997 | Faccioli et al. | |
| 5,766,179 A | 6/1998 | Faccioli et al. | |
| 5,935,127 A | 8/1999 | Border | |
| 6,027,506 A | 2/2000 | Faccioli et al. | |
| 7,077,847 B2 | 7/2006 | Pusnik et al. | |
| 7,094,242 B2 * | 8/2006 | Ralph et al. | 606/96 |
| 2004/0138671 A1 | 7/2004 | Zander et al. | |
| 2010/0160913 A1 * | 6/2010 | Scaglia | 606/57 |
| 2010/0179550 A1 * | 7/2010 | Schreiber et al. | 606/62 |

FOREIGN PATENT DOCUMENTS

| | | |
|---|---|---|
| EP | 0 514 662 | 11/1992 |
| EP | 1 344 494 | 9/2003 |
| EP | 1 415 599 | 5/2004 |

* cited by examiner

*Primary Examiner* — Ralph Lewis
(74) *Attorney, Agent, or Firm* — Maginot, Moore & Beck

(57) ABSTRACT

An adjustable angle targeting device for an intramedullary nail includes a frame, a drill guide, and a holding member with both the drill guide and the holding member supported by the frame. The holding member includes a spherical upper surface, a lower surface, a first rotational alignment member for aligning the intramedullary nail with the holding member, and a bore extending through the holding member. The bore includes a circular lower portion opening to the lower surface and a slot shaped upper portion opening to the upper surface and having a length greater than the diameter of the circular lower portion. The targeting device further includes a holding bolt for insertion through the bore. The holding bolt includes a coupling portion for coupling with the intramedullary nail and axially aligning the intramedullary nail and a head with a bottom surface shaped complementary to the upper surface of the holding member.

22 Claims, 9 Drawing Sheets

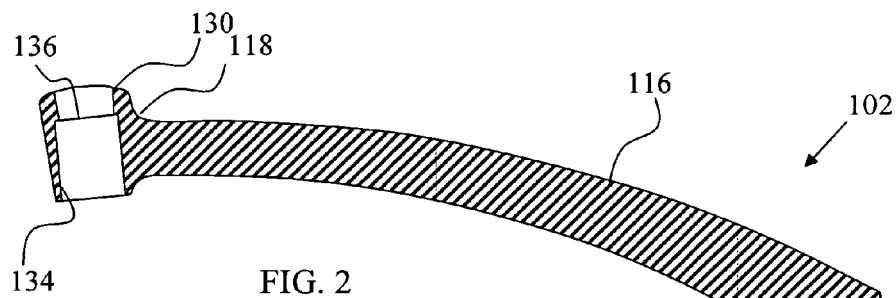
FIG. 2
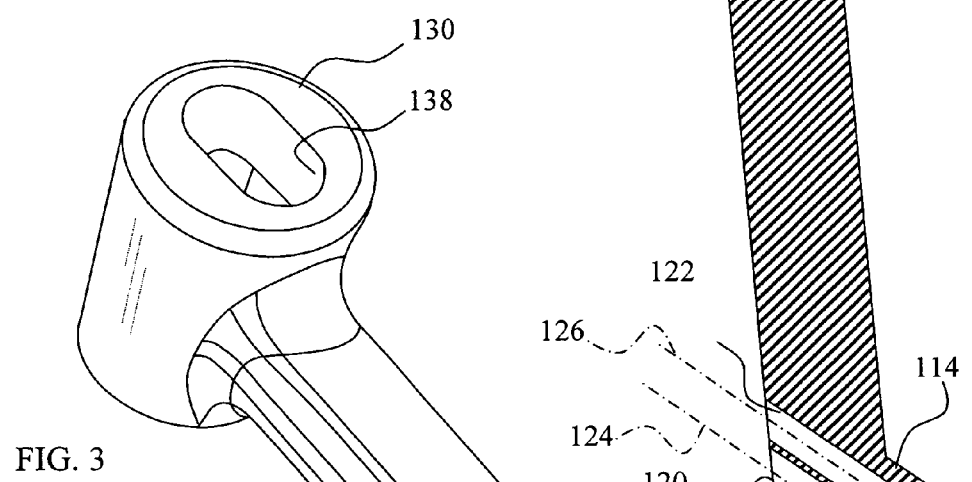
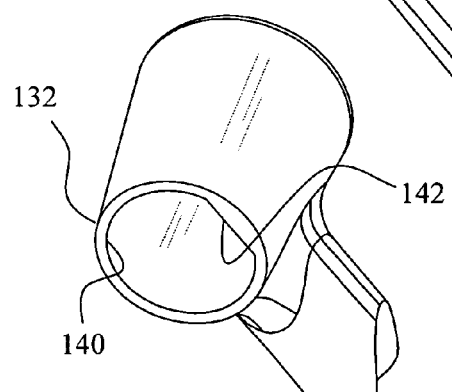
FIG. 3
FIG. 4

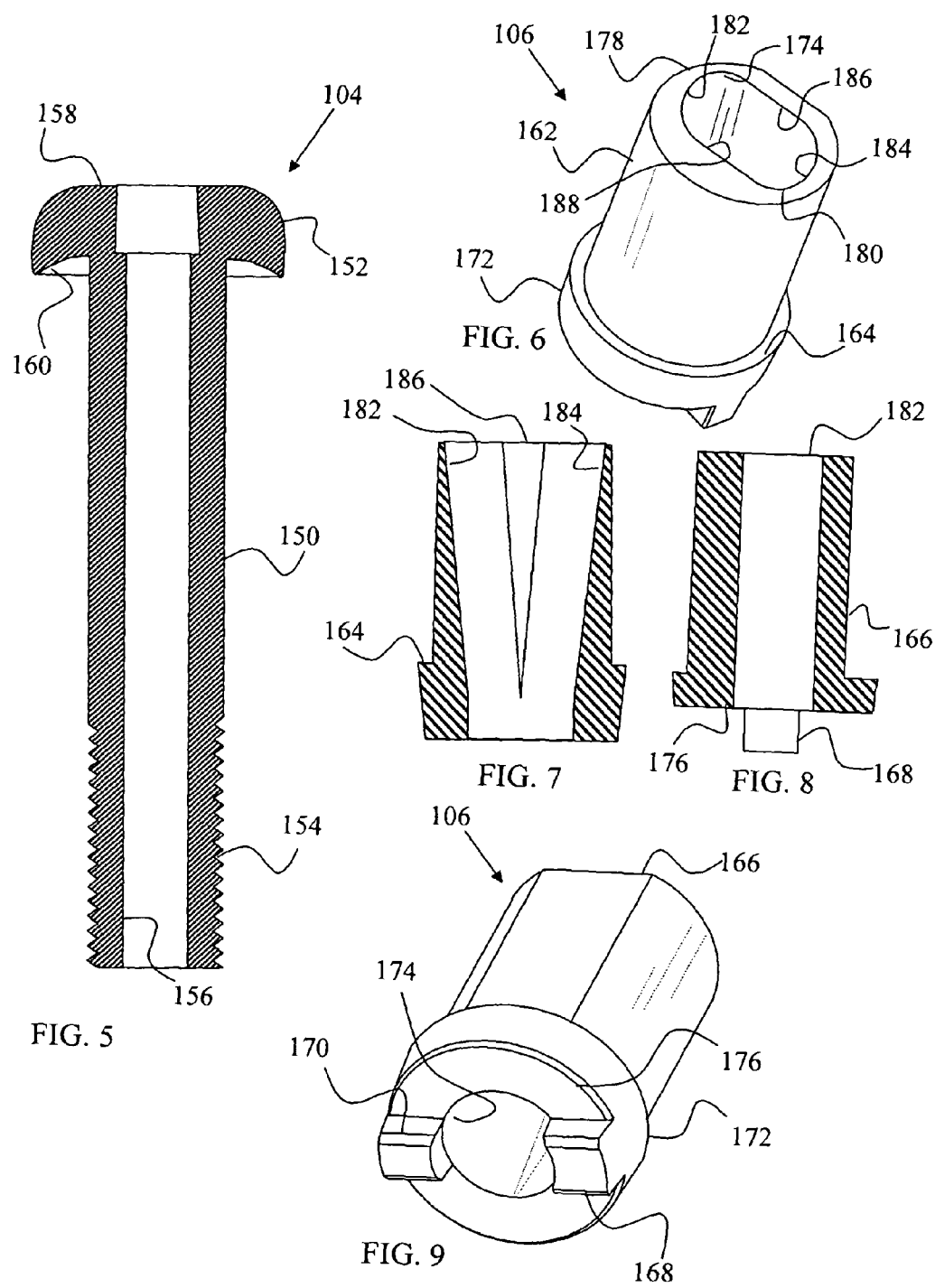

ADJUSTABLE ANGLE TARGETING DEVICE FOR AN INTRAMEDULLARY NAIL AND METHOD OF USE

FIELD

The present invention relates to implantation and fixation of intramedullary nails and, more particularly, to a bone fastener targeting device and method of use for implantation and fixation of an intramedullary nail

BACKGROUND

Intramedullary nails of the type used herein have two or more spaced holes or bores that extend diametrically across the intramedullary nail. These holes or bores are formed in the nail to accept or allow bone screws or fasteners to extend therethrough in order to fix the intramedullary nail to a bone or various bone fragments for the healing process. Since the fasteners are installed after the intramedullary nail has been inserted into the patient, such bone screw holes or bores are said to be "blind" in terms of bone-drilling alignment that must be achieved. Since the intramedullary nail is implanted into the patient, a problem exists with assuring correct alignment for drilling through the bone in order that a screw placed through the drilled hole also goes through a correct hole of the intramedullary nail.

Because of this problem, many devices have been devised that aid in assuring correct alignment of bone screws and the intramedullary nail. It has been recognized by inventors of these devices that one method of determining where the intramedullary nail is located within the bone is to manufacture the device from radiolucent materials that allow radiographs to be made. In connection with this problem, other devices have been designed to pivot out of the way to allow radiographs to be made. Additionally, surgeons often also use external fixation devices to maintain alignment and length.

In view of the above, what is thus needed is an improved system of targeting bone fasteners for alignment with holes in the intramedullary nail.

SUMMARY

In one embodiment, an adjustable angle targeting device includes a holding member with a spherical upper surface and a lower surface, a first rotational alignment member for rotationally aligning an intramedullary nail with the holding member, a bore extending through the holding member and including a circular lower portion opening to the lower surface and a slot shaped upper portion opening to the upper surface, the slot having a length greater than the diameter of the circular lower portion, and a holding bolt for insertion through the bore and including (i) a shaft portion having a length greater than the length of the bore and a diameter less than the diameter of the circular lower portion, (ii) a coupling portion for coupling with the intramedullary nail and axially aligning the intramedullary nail, and (iii) a head with a bottom surface shaped complementary to the upper surface of the holding member.

In another embodiment, an intramedullary nail targeting kit includes a frame, a holding member supported by the frame, the holding member including a bore with a slot portion and a circular portion, a coupling member configured to extend through the bore and to pivot with respect to the holding member within the slot portion and about the circular portion of the bore in a pivot plane, a drill guide supported by the frame and having a longitudinal axis extending within the pivot plane, and a plurality of intramedullary nails, each of the plurality of intramedullary nails including a coupling portion for coupling with the coupling member and a rotational alignment member for rotational alignment with the holding member.

In yet another embodiment a method of targeting an intramedullary nail includes selecting an intramedullary nail, rotationally aligning a bore axis of the intramedullary nail within a pivot plane defined by a slot portion and a circular portion of a bore in a holding member, positioning a portion of a coupling member within the slot portion and the circular portion of the bore, coupling the intramedullary nail with the positioned coupling member in a fixed axial relationship, rotationally fixing the rotationally aligned intramedullary nail with respect to the pivot plane, pivoting the coupled coupling member and intramedullary nail within the pivot plane, aligning the bore axis with a drill guide axis to target the intramedullary nail, and clamping the targeted intramedullary nail.

BRIEF DESCRIPTION OF THE DRAWINGS

FIG. 2 depicts a cross sectional view of the targeting device of FIG. 1 showing a holder with a bore including a slot shaped upper portion opening to a spherically shaped upper surface and a circular lower portion, and a drill guide;

FIGS. 3 and 4 depict partial perspective views of the targeting device of FIG. 1 showing the holder with a slot shaped upper bore portion and circular lower bore portion with a key in the form of a flat surface;

FIG. 5 depicts a cross sectional view of the coupling member of FIG. 1 which in this embodiment is a bolt having a head with a spherically shaped lower surface, and a shaft with a threaded portion;

FIG. 6 depicts a top perspective view of the coupler of FIG. 1, which is a component along with the holder of FIGS. 3 and 4 of a holding member, with a slot shaped upper bore portion and a circular lower portion;

FIG. 7 depicts a cross sectional view of the coupler of FIG. 1 showing the flat side of the slot tapering to the circular lower portion;

FIG. 8 depicts a cross sectional view of the coupler of FIG. 1 showing a curved end of the bore and a protuberance for rotationally aligning the coupler with an intramedullary nail;

FIG. 9 depicts a bottom perspective view of the coupler of FIG. 1 showing a tapered outer wall with a key in the form of a flat surface for rotationally aligning the coupler with the holder of FIGS. 3 and 4 and two protuberances for rotationally aligning the coupler with an intramedullary nail;

FIG. 20 depicts the clamped intramedullary nail of FIG. 15 after aligning the fastener bore axis with the drill guide axis of the targeting device;

DETAILED DESCRIPTION

Figure 1:
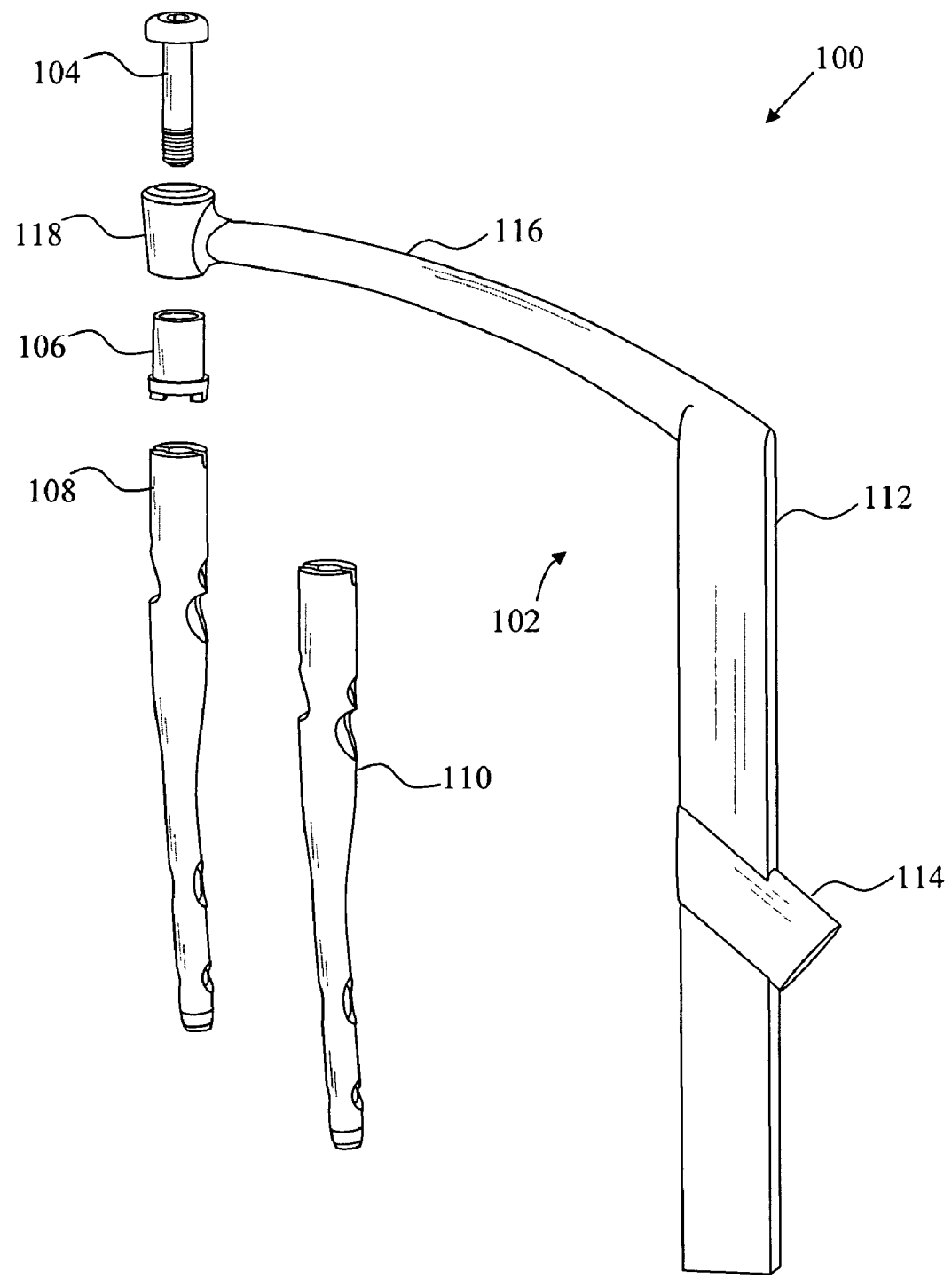
FIG. 1 depicts a perspective view of a targeting system including a targeting device, a coupler, a coupling member and two intramedullary nails having different nail angles in accordance with principles of the invention.

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

A targeting system 100 is shown in FIG. 1. The targeting system 100 includes a targeting device 102, a coupling member 104, a coupler 106, and two intramedullary nails 108 and 110. The targeting device 102 includes a frame 112 with a guide portion 114. An arm 116 extends from the frame 112 and supports a holder 118.

With reference to FIG. 2, the guide 114 includes a drill guide 120 and a targeting guide 122. The drill guide 120 and the targeting guide 122 have parallel longitudinal axes 124 and 126, respectively.

The holder 118 is shown in FIGS. 2-4. The holder 118 includes a spherically shaped upper surface 130 and a circular lower surface 132. A bore 134 extends between the upper surface 130 and the lower surface 132. A ledge 136 in the bore 134 separates an upper bore 138 from a lower bore 140. The upper bore 138 opens to the upper surface 130 as an elongated slot as most clearly shown in FIG. 3. The lower bore 140 opens to the lower surface 132 in the form of a circular opening with the exception of a flat portion 142 that extends upwardly from the lower surface 132.

The coupling member 104, shown in FIG. 5 as a holding bolt, includes a shaft 150 and a head 152. The shaft 150 includes a coupling portion, such as threaded portion 154. A bore 156 extends completely through the shaft 150 and opens to the upper surface 158 of the head 152. The lower surface 160 of the head 152 is spherically shaped on a radius complimentary to the radius of the spherical upper surface 130 of the holder 118.

The coupler 106 is shown in FIGS. 6-9. The coupler 106 includes a tapered outer wall 162 which terminates at a ledge 164. The outer wall 162 is substantially circular in cross section with the exception of a flat portion 166. A first rotational alignment member, such as protuberances 168 and 170, extends from a skirt 172 located below the ledge 164. A bore 174 extends from the lower surface 176 of the skirt 172 to the upper surface 178 of the coupler 106. The opening of the bore 174 to the lower surface 176 is circular while the opening of the bore 174 to the upper surface 178 forms an elongated slot 180. The elongated slot 180 includes two end curves 182 and 184 that are formed with the same radius as the opening of the bore 174 to the lower surface 176. Two sides 186 and 188 extend between the end curves 182 and 184. The sides 186 and 188 taper inwardly and downwardly within the bore 174 as best seen in FIG. 7.

Figures 10, 11, 12:
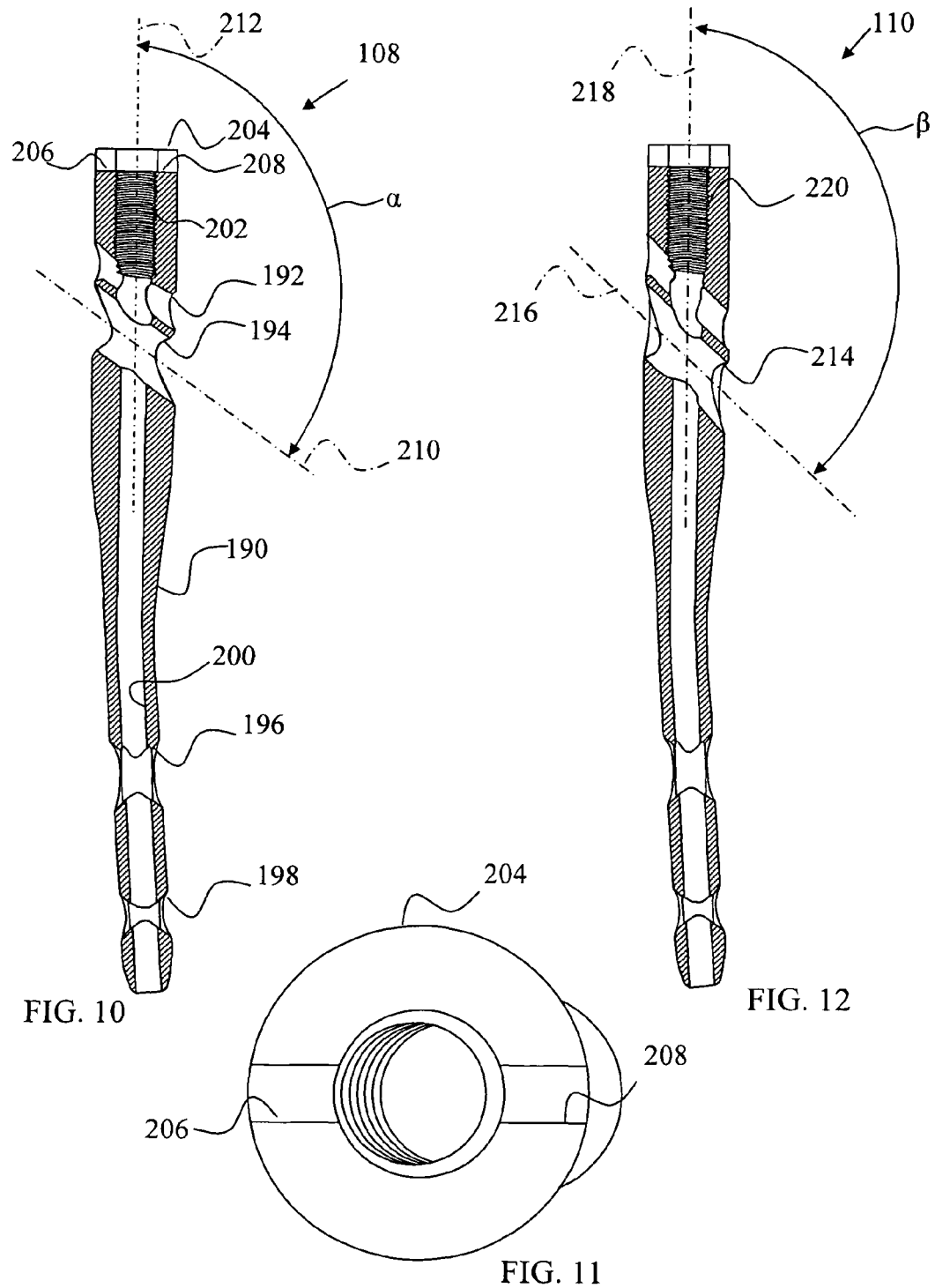
FIG. 10 depicts a cross sectional view of one of the intramedullary nails of FIG. 1 showing a nail angle between the axis of the threaded upper portion of a bore and the axis of a fastener bore.
FIG. 11 depicts a top plan view of the intramedullary nail of FIG. 10 showing a head with two slots for rotationally aligning the intramedullary nail with the coupler of FIG. 1.
FIG. 12 depicts a cross sectional view of one of the intramedullary nails of FIG. 1 showing a nail angle between the axis of the threaded upper portion of a bore and the axis of a fastener bore that is different from the nail angle of the intramedullary nail of FIG. 10.

The intramedullary nail 108 shown in FIGS. 10 and 11 includes a shaft 190 with transaxial bores 192, 194, 196, and 198. A bore 200 extends along the length of the intramedullary nail 108. The bore 200 includes a threaded portion 202 and opens to the head 204 of the intramedullary nail 108. Two slots 206 and 208 are located in the head 204. The bore 194 is configured to receive a lag screw (not shown) and is formed with a centerline 210 that intersects the centerline 212 of the threaded portion 202 at an angle $\alpha$, also referred to herein as a nail angle, of about 125 degrees. The intramedullary nail 110 shown in FIG. 12 is substantially identical to the intramedullary nail 108 with the exception that a bore 214 which is configured to receive a lag screw (not shown) is formed with a centerline 216 that intersects the centerline 218 of the threaded portion 220 at an angle $\beta$ of about 130 degrees.

With reference to the foregoing figures, the targeting system 100 may be used by initially preparing a femur to receive an intramedullary nail in accordance with a desired procedure. Once the surgical site is properly prepared, an intramedullary nail is selected based upon, in part, the angle between the axis of the femoral neck and the axis of the femoral diaphysis. For this example, the intramedullary nail 108 will be used. As with many of the actions described herein, the order of the actions may be varied. Thus, the selected intramedullary nail may first be implanted or the intramedullary nail may first be attached to the targeting device 102.

In either case, the protuberances 168 and 170 of the coupler 106 are aligned with the slots 206 and 208 on the head 204 of the intramedullary nail 108. The protuberances 168 and 170 are sized to fit within the slots 206 and 208. Accordingly, once the protuberances 168 and 170 are aligned with the slots 206 and 208, the protuberances 168 and 170 are inserted into the slots 206 and 208, respectively.

Figure 13:
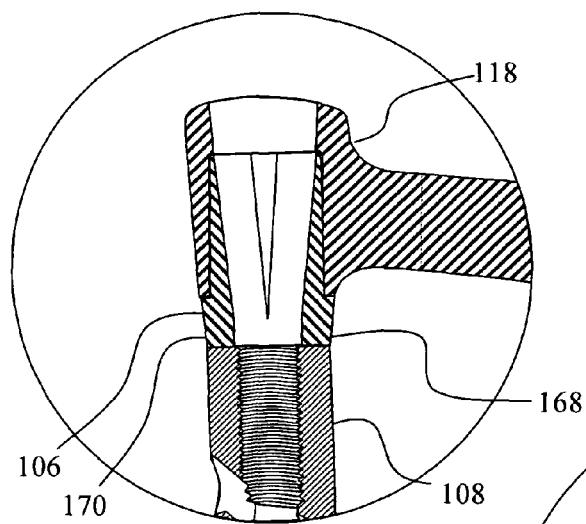
FIGS. 13-15 depict the coupling member of FIG. 1 used to clamp one of the intramedullary nails of FIG. 1 to the coupler and targeting device of FIG. 1.

Next, the holder 118 is aligned with the coupler 106. More specifically, the flat portion 166 of the coupler 106 is aligned with the flat portion 142 of the holder 118. The upper surface 178 of the coupler 106 is then inserted into the bore 134. The height of the tapered outer wall 162 corresponds to the distance from the lower surface 132 of the holder 118 to the ledge 136 within the bore 134. Additionally, the diameter of the ledge 164 is greater than the diameter of the lower bore 140 of the holder 118 and the diameter of the upper surface 178 is greater than the diameter of the bore 134 at the ledge 136. Accordingly, as the upper surface 178 abuts the ledge 136, the ledge 164 abuts the lower surface 132 of the holder 118 resulting in the configuration shown in FIG. 13.

Figure 14:
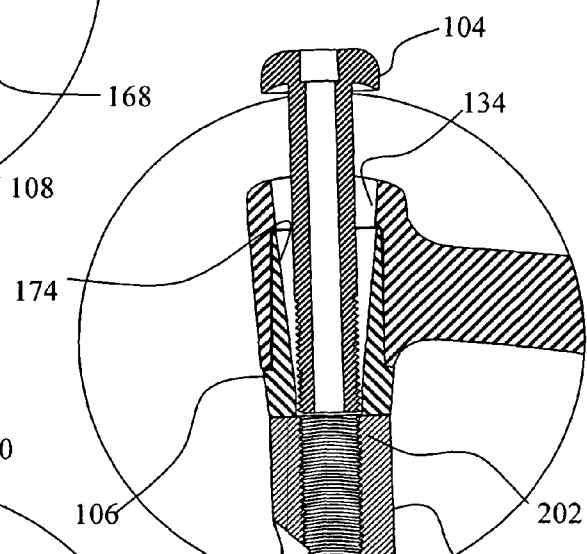
Figure 15:
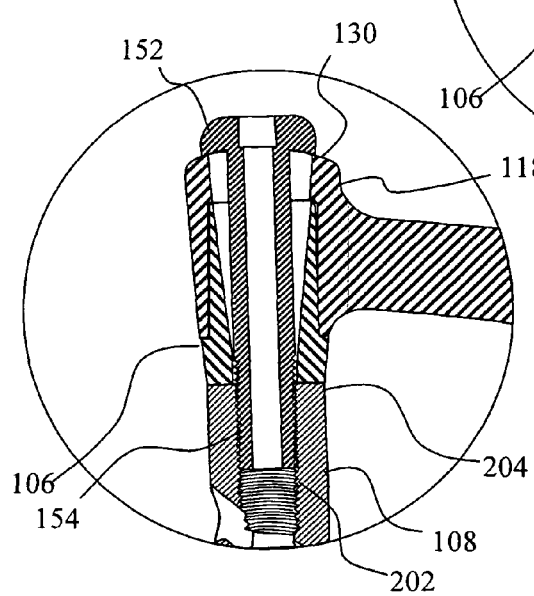

The bolt 104 is then inserted through the bore 134 of the holder 118 and through the bore 174 of the coupler 106 as shown in FIG. 14. Engaging the threaded portion 154 of the bolt 104 with the threaded portion 202 of the intramedullary nail 108 provides the configuration of FIG. 15. In FIG. 15, the intramedullary nail 108 is pulled tightly against the coupler 106 which is, in turn, held firmly against the holder 118. The assembly is thus clamped between the head 152 of the bolt 104 and the head 204 of the intramedullary nail 108.

Figure 16:
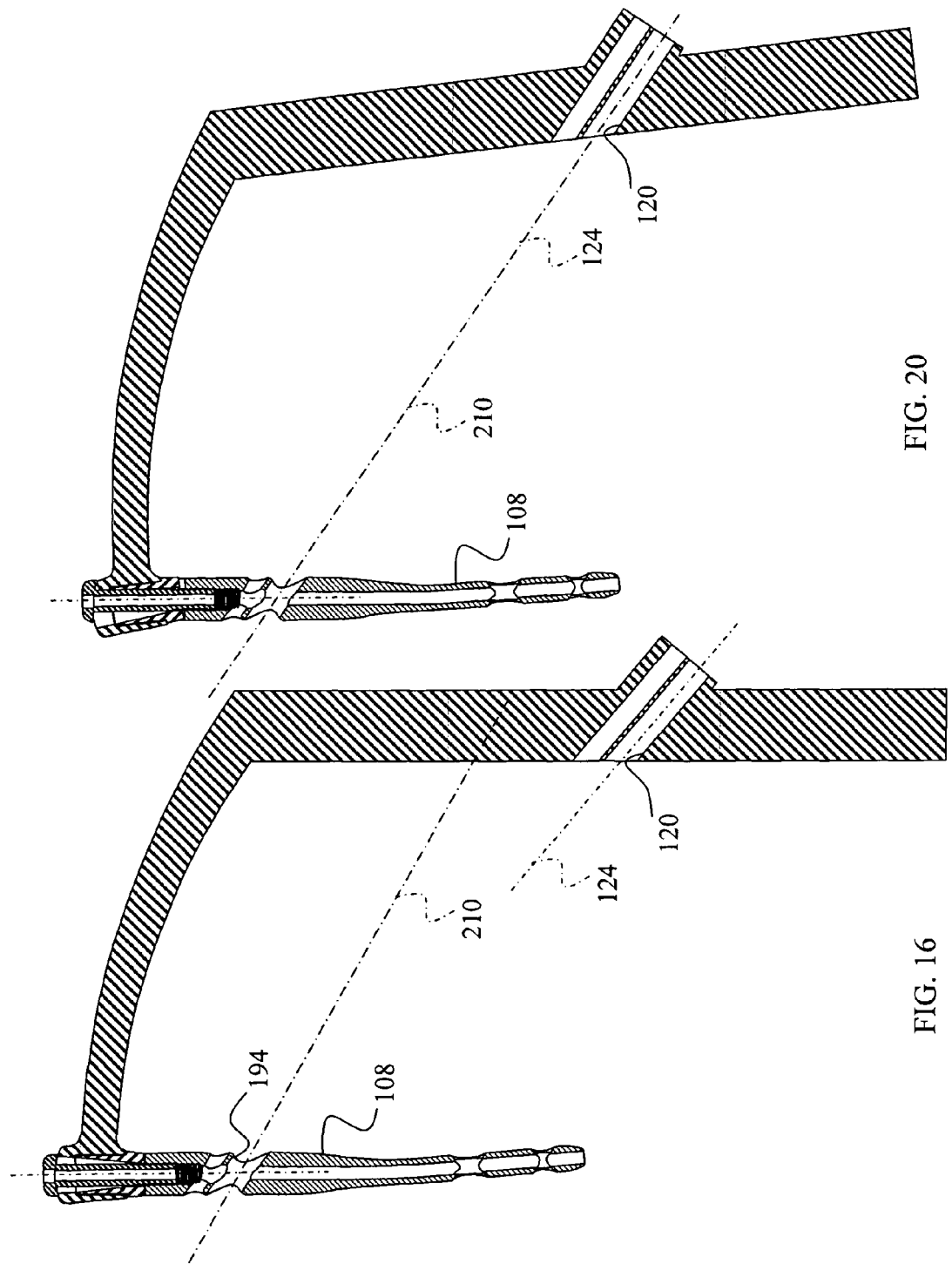
FIG. 16 depicts the clamped intramedullary nail of FIG. 15 with the fastener bore axis out of alignment with the drill guide axis of the targeting device.
Figure 17:
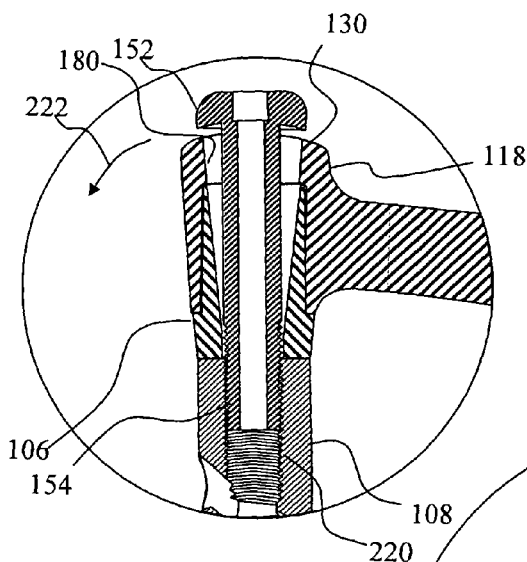
FIGS. 17-19 depict pivoting of the axially aligned coupling member and intramedullary nail relative to the targeting device wherein the coupling member pivots within the slotted bore portion of the holding member and about the circular bore portion of the holding member to change the alignment of the fastener bore axis with respect to the drill guide axis of the targeting device while maintaining the rotational alignment of the coupling member and intramedullary nail relative to the targeting device.

When the intramedullary nail 108 is clamped in this manner, the axis or centerline 210 of the bore 194 is not aligned with the axis 124 of the drill guide 120 as shown in FIG. 16. Alignment is enabled by backing the bolt 104 out of the threaded portion 202 to the position shown in FIG. 17. In FIG. 17, the system 100 is not tightly clamped. Accordingly, because the upper surface 130 of the holder 118 and the lower surface 160 of the head 152 are both spherically shaped with the same radius of curvature, the targeting device 102 and the coupler 106 may be pivoted in the direction of the arrow 222 with respect to the bolt 104 and the intramedullary nail 108. The radius of curvature for the upper surface 130 of the holder 118 and the radius of curvature for the lower surface 160 of the head 152 need not be identical. Increased clamping surface, however, is realized as the radii of curvature are matched more closely.

The bolt 104 thus moves along the slot 180 of the coupler 106 within the upper bore 138 of the holder 118. The bolt 104 is thus pivoted with respect to the slot 180 as it pivots about the circular portion of the bore 174.

Figure 18:
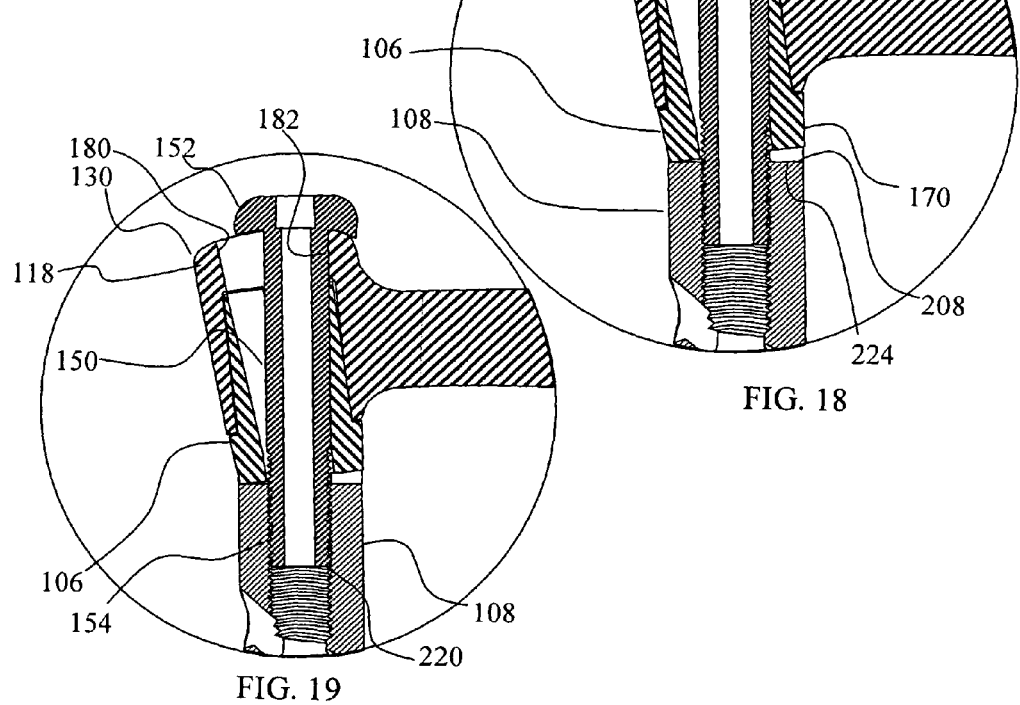
Figure 19:
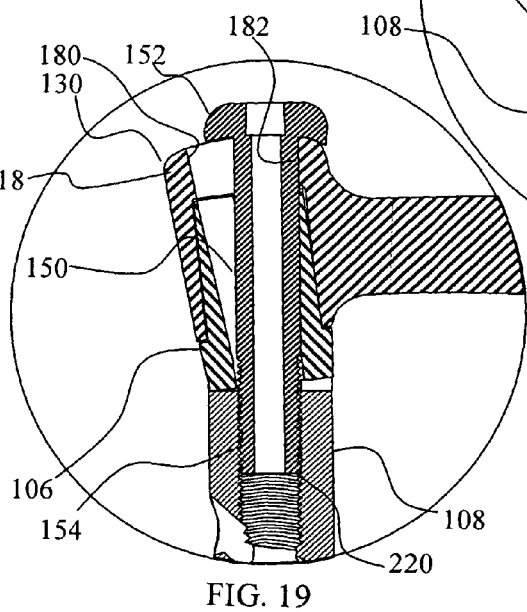

Pivoting the targeting device 102 and the coupler 106 in the direction of the arrow 222 pivots the protuberance 170 partially out of the slot 208 resulting in a gap 224 between the coupler 106 and the intramedullary nail 108 shown in FIG. 18. Once the targeting device 102 and the coupler 106 have been pivoted to the desired location along the slot 180, the bolt 104 is threaded into the threaded portion 202 of the intramedullary nail 108 which provides the configuration of FIG. 19. In FIG. 19, the intramedullary nail 108 is again pulled tightly against the coupler 106 which is, in turn, held firmly against the holder 118. The assembly is thus clamped between the head 152 of the bolt 104 and the head 204 of the intramedullary nail 108 with a different alignment between the targeting device 102 and the intramedullary nail 108.

Pivoting the targeting device 102 and the coupler 106 thus adjusts the alignment between the centerline 210 of the bore 194 and the axis 124 of the drill guide 120. Consequently the length of the slot 180 limits the amount by which the alignment may be modified. In other words, the intersection of the axes defined by each of the end curves 182 and 184 with the axis 124 of the drill guide 120 define the limiting nail angles that can be aligned with the drill guide 120. In this embodiment, the length of the slot 180 is selected such that when the shaft 150 of the bolt 104 is positioned against the end curve 182 as shown in FIG. 19, the centerline 210 of the bore 194 and the axis 124 of the drill guide 120 are aligned as shown in FIG. 20.

If desired, flats may also be formed on the protuberances 168 and 170 to provide increased clamping surface. Additionally, the coupler 106 and the holder 118 may be formed as an integral holding member. When the coupler 106 and the holder 118 are formed as an integral holding member, the holding member retains the same structural attributes as if the coupler 106 and the holder 118 were joined together. For example, the holding member retains the spherical upper surface 130 and the upper bore 138 of the holder 118. The holding member also retains the inwardly tapering sides 186 and 188 forming the lower bore and the protuberances 168 and 170 of the coupler 106. When the coupler 106 and the holder 118 are formed as separate components of a holding member, the holder 118 may be manufactured from a metal material and the targeting device 102 formed from a carbon fiber or other radiolucent material.

Figure 22:
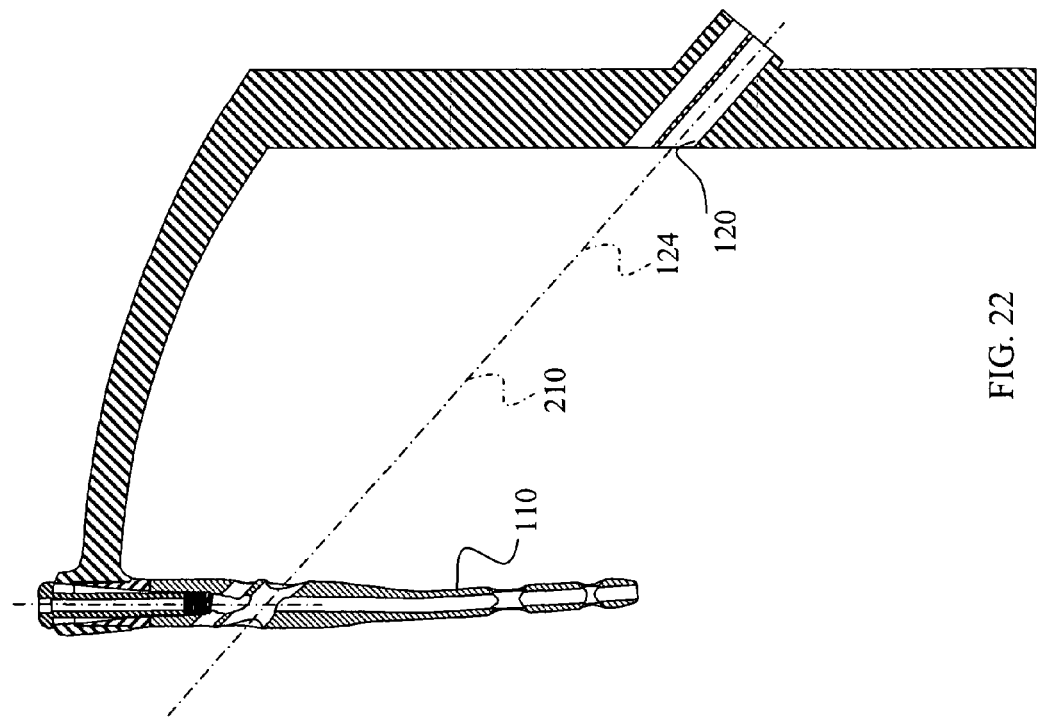
FIG. 22 depicts the clamped intramedullary nail of FIG. 21 after aligning the fastener bore axis with the drill guide axis of the targeting device by locating the coupling member in the middle of the slotted bore of the holding member.

Coupling of the intramedullary nail 110 is accomplished in significantly the same manner as discussed above with respect to the intramedullary nail 108. The axis or centerline 216 of the bore 214, however, is oriented at a larger angle with respect to the axis of the threaded portion 220 than the centerline 210 of the bore 194 is oriented with respect to the axis of the threaded portion 202. Thus, once the intramedullary nail 110 is positioned with the holding bolt 104 located in the center of the slot 178 as shown in FIG. 21, the centerline 216 of the bore 214 is aligned with the axis 124 of the drill guide 120 as shown in FIG. 22.

Figure 21:
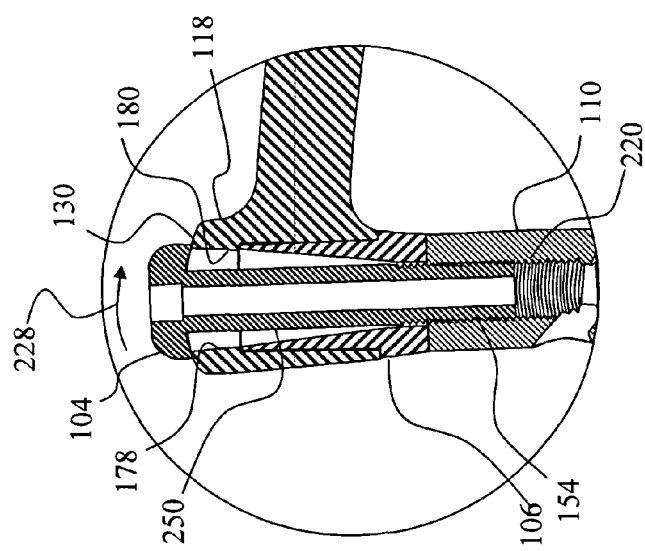
FIG. 21 depicts the coupling member of FIG. 1 used to clamp one of the intramedullary nails of FIG. 1 to the coupler and targeting device of FIG. 1.

As is evident from FIG. 21, the slot 180 is configured in this embodiment to provide further pivoting of the targeting device 102 and coupler 106 in the direction of the arrow 228. Accordingly, the system 100 may further include an intramedullary nail (not shown) with an angle of about 135 degrees between a bore axis and the axis of a threaded portion which could be aligned with the axis 124 of the drill guide 120. In alternative embodiments, the targeting system may be configured to align intramedullary nails configured within a larger or smaller range of angles.

In alternative embodiments, the centerline 210 of the bore 194 and the axis 124 of the drill guide 120 are automatically aligned as the intramedullary nail 108 is clamped to the targeting device 102 by the holding screw 104. In such embodiments, a base clamping angle between a plane defined by a first clamping component of the coupler 106 and the axis 124 of the drill guide 120 is established. A nail clamping angle between a plane defined by a second clamping component of the intramedullary nail 108 and the axis 212 of the threaded portion 202 is then selected such that the sum of the base clamping angle and the nail clamping angle is equal to the angle between the axis 212 of the threaded portion 202 and the centerline 210 of the bore 194.

By way of example, a base clamping angle may be 40 degrees. Thus, the first clamping component of the coupler, such as the lower surface 176 of the skirt 172 or the bottom of the protuberances 168 and 170, is configured to define a plane which intersects the axis 124 of the drill guide 120 at an angle of 40 degrees. Since the intramedullary nail 108 has a nail angle of 125 degrees, the nail clamping angle must be 85 degrees. Accordingly, the second clamping component, such as the upper surface of the head 204 if the lower surface 176 is a clamping component, or the bottom of one or both of the slots 206 and 208 if the bottom of one or both of the protuberances 168 and 170 is a clamping component, is configured to define a plane which intersects the axis 212 of the threaded portion 202 at an angle of 85 degrees.

Thus, when the second clamping component of the intramedullary nail 108 is clamped against the first clamping component of the coupler 106, the intramedullary nail 108 will be forced into a position where the centerline 210 of the bore 194 and the axis 124 of the drill guide 120 are aligned. For intramedullary nails having different nail angles, each intramedullary nail may be provided with a different nail clamping angle for use with a single coupler, or a variety of couplers with different base clamping angles may be used with intramedullary nails with different nail angles but the same nail clamping angle to provide automatic alignment. In these alternative embodiments, the intersection of the axes defined by each of the end curves 182 and 184 with the axis 124 of the drill guide 120 maybe selected to be larger than the nail angles to be used with the device.

Figure 23:
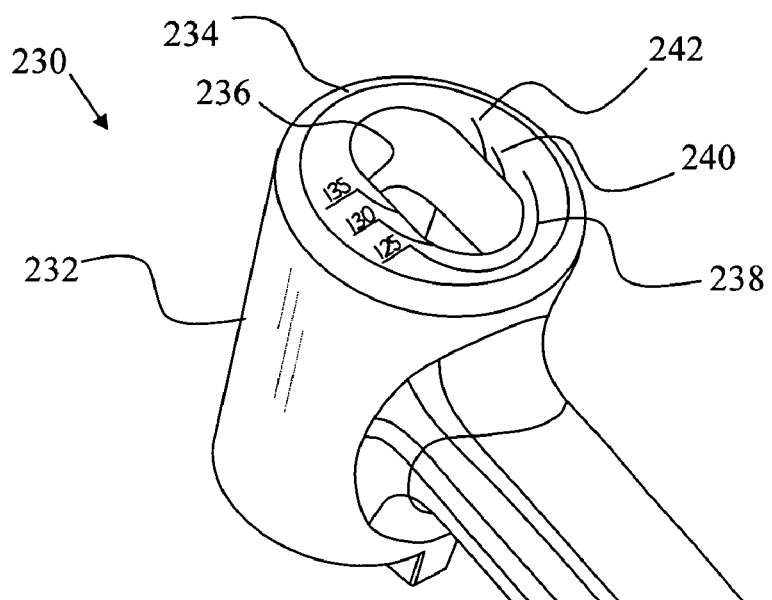
FIGS. 23 and 24 depict partial views of an alternative embodiment of a targeting device wherein the holding member includes a coupler component integrally formed with a holder component and markings on the spherical upper surface of the holding member to assist in aligning the drill guide axis with intramedullary nails having various nail angles.
Figure 24:
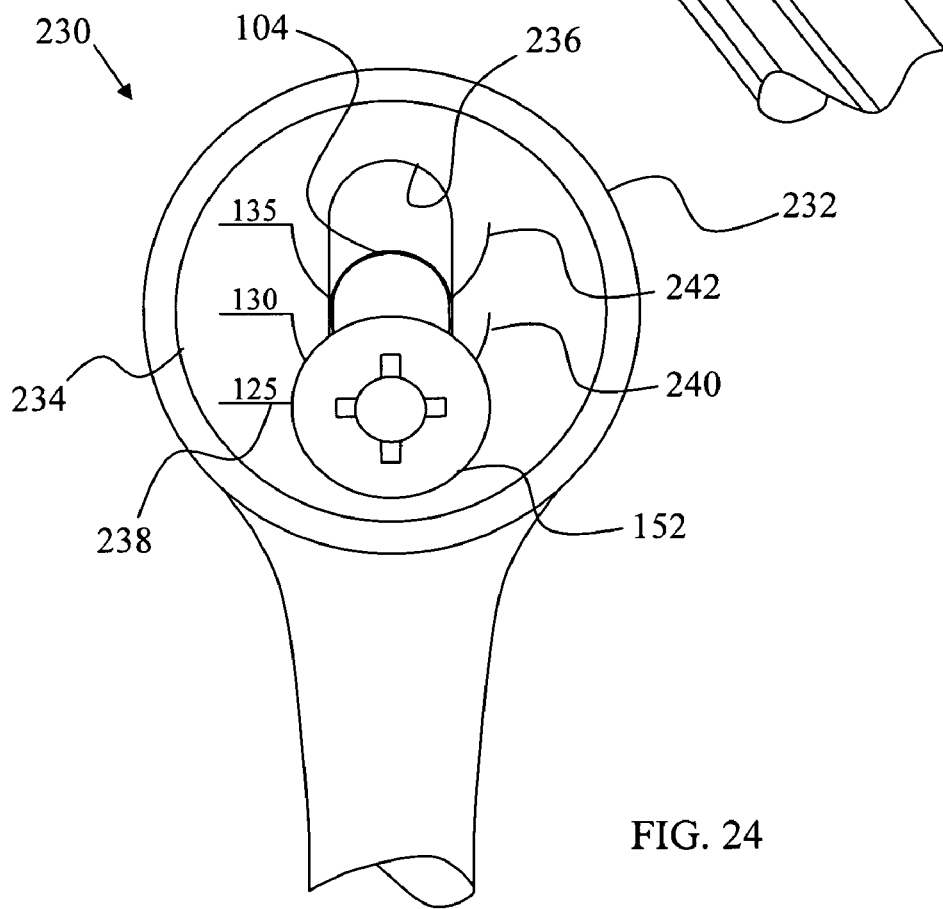

An alternative embodiment of a targeting device 230 is shown in FIG. 23. The targeting device 230 includes an integrally formed holding member 232 with a spherically curved upper surface 234 and a slot 236. Markings 238, 240, and 242 are located on the spherical surface 234. The targeting device 230 is in all other ways substantially identical to the targeting device 102. The markings 238, 240, and 242 provide references for aligning the bore axes of three different intramedullary nails (not shown) with the drill guide (not shown) of the targeting device 230. By way of example, aligning the head 152 of the bolt 104 with the mark 238 may align the bore axis of a 125 degree intramedullary nail as shown in FIG. 24. Similarly, the marks 240 and 242 may be used to align a 130 degree intramedullary nail and a 135 degree intramedullary nail, respectively. Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the embodiments contained herein.

What is claimed is:

1. A targeting device for an intramedullary nail comprising:
   a frame;
   a drill guide supported by the frame;
   a holding member supported by the frame, the holding member including a spherical upper surface, a lower surface, and a first rotational alignment member for rotationally aligning an intramedullary nail with the holding member;
   a bore extending through the holding member and including a circular lower portion opening to the lower surface and a slot shaped upper portion opening to the upper surface, the slot having a length along the upper surface greater than the diameter of the circular lower portion; and
   a holding bolt for insertion through the bore and including (i) a shaft portion having a length greater than the length of the bore and a diameter less than the diameter of the circular lower portion, (ii) a coupling portion for coupling with the intramedullary nail and axially aligning the intramedullary nail, and (iii) a head with a bottom surface shaped complementary to the upper surface of the holding member.

2. The device of claim 1, wherein:
   the holding member comprises
      a holder with a first bore portion, and
      a coupler with a second bore portion, the coupler keyed to removably mate with the holder in a rotationally fixed alignment; and
   the bore comprises the first bore portion and the second bore portion.

3. The device of claim 2, wherein:
   the upper surface of the holder comprises the spherical upper surface;
   the first rotational alignment member comprises at least one protuberance extending from the coupler; and
   an outer surface of the coupler is configured to removably mate with a cavity in the holder.

4. The device of claim 3, wherein:
   the drill guide defines a longitudinal axis; and
   the slot is coplanar with the longitudinal axis such that the holding bolt is positionable within the slot with the longitudinal axis of the bolt at any one of a plurality of angles with respect to the longitudinal axis of the drill guide.

5. The device of claim 4, wherein:
   a first end portion of the slot defines an axis which intersects the longitudinal axis of the drill guide at an angle of about 125 degrees; and
   a second end portion of the slot defines an axis which intersects the longitudinal axis of the drill guide at an angle of about 135 degrees.

6. The device of claim 1, wherein the holding bolt is configured to axially align with the intramedullary nail when the holding bolt is coupled with the intramedullary nail.

7. The device of claim 1 wherein the spherical upper surface and the bottom surface of the head of the holding bolt are formed with the same radius of curvature.

8. An intramedullary nail targeting kit comprising:
   a frame;
   a holding member supported by the frame, the holding member including a bore with a slot portion and a circular portion;
   a coupling member configured to extend through the bore and to pivot with respect to the holding member within the slot portion and about the circular portion of the bore in a pivot plane;
   a drill guide supported by the frame and having a longitudinal axis extending within the pivot plane; and
   a plurality of intramedullary nails, each of the plurality of intramedullary nails including a coupling portion for coupling with the coupling member and a rotational alignment member for rotational alignment with the holding member.

9. The kit of claim 8, wherein:
   the coupling portion for each of the plurality of intramedullary nails defines an axis and is configured to axially align with the coupling member when the coupling portion is coupled with the coupling member;
   each of the plurality of intramedullary nails includes a bore having a bore axis which intersects the axis of the coupling portion to define a nail angle; and
   the nail angle of each of the plurality of intramedullary nails is different from the nail angle of each of the other of the plurality of intramedullary nails.

10. The kit of claim 9, wherein the slot portion comprises:
    a first end portion defining a first slot axis in the pivot plane; and
    a second end portion defining a second slot axis in the pivot plane, wherein:
    the first slot axis intersects the drill guide axis at a first limiting angle;
    the second slot axis intersects the drill guide axis at a second limiting angle;
    the first limiting angle is larger than the second limiting angle; and
    none of the nail angles for the plurality of intramedullary nails is larger than the first limiting angle or smaller than the second limiting angle.

11. The kit of claim 9, wherein:
    the holding member comprises a first clamping component defining a base clamping angle;
    each of the plurality of intramedullary nails comprises a second clamping component defining a respective nail clamping angle; and the nail clamping angle for each of the plurality of intramedullary nails is selected such that the sum of the nail clamping angle and the base clamping angle is equal to the nail angle of each of the respective one of the plurality of intramedullary nails.

12. The kit of claim 8, wherein the coupling member comprises:
a threaded portion configured to engage the coupling portion of each of the plurality of intramedullary nails; and
a head portion configured to engage a portion of the holding member, the coupling member configured to releasably clamp each of the plurality of intramedullary nails to the holding member.

13. The kit of claim 12, wherein:
the holding member comprises at least one protuberance; and
the rotational alignment member of each of the plurality of intramedullary nails comprises at least one slot for receiving the at least one protuberance.

14. The kit of claim 8 wherein:
the holding member comprises a holder and a coupler, the coupler configured to be received within a cavity in the holder in a keyed relationship;
the slot portion is location within the holder;
the circular portion is located within the coupler;
the coupler comprises at least one protuberance; and
the rotational alignment member of each of the plurality of intramedullary nails comprises at least one slot for receiving the at least one protuberance.

15. A method of targeting an intramedullary nail comprising:
selecting an intramedullary nail;
rotationally aligning a bore axis of the intramedullary nail within a pivot plane defined by a slot portion and a circular portion of a bore in a holding member;
positioning a portion of a coupling member within the slot portion and the circular portion of the bore;
coupling the intramedullary nail with the positioned coupling member in a fixed axial relationship;
rotationally fixing the rotationally aligned intramedullary nail with respect to the pivot plane;
pivoting the coupled coupling member and intramedullary nail within the pivot plane;
aligning the bore axis with a drill guide axis to target the intramedullary nail; and
clamping the intramedullary nail to the holding member.

16. The method of claim 15, wherein coupling the intramedullary nail with the coupling member comprises:
engaging a threaded portion of an internal bore of the intramedullary nail with a threaded portion of the coupling member.

17. The method of claim 15, wherein rotationally fixing the rotationally aligned intramedullary nail comprises:
engaging a slot in the intramedullary nail with a protuberance extending from the holding member.

18. The method of claim 17, wherein pivoting the coupled coupling member and intramedullary nail within the pivot plane comprises:
pivoting the protuberance with respect to the slot.

19. The method of claim 15, wherein;
selecting an intramedullary nail comprises selecting an intramedullary nail having a nail angle of between about 125 degrees and about 135 degrees.

20. The method of claim 15, wherein clamping the intramedullary nail comprises:
rotating a threaded portion of the coupling member within a threaded portion of an internal bore of the intramedullary nail; and
engaging an upper surface of the holding member with a head portion of the coupling member.

21. The method of claim 20, wherein clamping the intramedullary nail further comprises:
engaging a spherical upper surface of the holding member with a spherical portion of a head portion of the coupling member.

22. The method of claim 15, wherein pivoting the coupled coupling member and intramedullary nail within the pivot plane, aligning the bore axis with a drill guide axis to target the intramedullary nail, and clamping the intramedullary nail comprise:
forcing a first clamping component of the holding member defining a base clamping angle against a second clamping component of the intramedullary nail defining a nail clamping angle, wherein the nail clamping angle for the intramedullary nail is selected such that the sum of the nail clamping angle and the base clamping angle is equal to the nail angle of the intramedullary nail.

* * * * *

UNITED STATES PATENT AND TRADEMARK OFFICE
CERTIFICATE OF CORRECTION

| | | |
|---|---|---|
| PATENT NO. | : 8,182,490 B2 | Page 1 of 1 |
| APPLICATION NO. | : 12/143443 | |
| DATED | : May 22, 2012 | |
| INVENTOR(S) | : Charles D. Christie | |

It is certified that error appears in the above-identified patent and that said Letters Patent is hereby corrected as shown below:

Column 1,
Line 10, after "nail" insert --.--

Column 3,
Line 38, replace "herein by" with --herein be--

Column 4,
Lines 2-3, replace "complimentary" with --complementary--

Column 9,
Line 25, replace "is location" with --is located--

Column 10,
Line 16, replace "wherein;" with --wherein:--

Signed and Sealed this
Twenty-sixth Day of February, 2013

Teresa Stanek Rea
*Acting Director of the United States Patent and Trademark Office*